(12) United States Patent
Von Oepen et al.

(10) Patent No.: US 7,875,067 B2
(45) Date of Patent: Jan. 25, 2011

(54) APPARATUS FOR DELIVERY AND DEPLOYMENT OF AN EXPANDABLE STENT WITHIN A BLOOD VESSEL

(75) Inventors: Randolf Von Oepen, Los Altos Hills, CA (US); Volker Trösken, Bochum (DE); Volker Marx, Hechingen (DE); Armin Stopper, Haigerloch (DE); Louise Balfe, Tübingen (DE); Lorcan Coffey, Tübingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 971 days.

(21) Appl. No.: 10/523,596

(22) PCT Filed: Aug. 7, 2003

(86) PCT No.: PCT/EP03/08795
§ 371 (c)(1),
(2), (4) Date: Dec. 2, 2005

(87) PCT Pub. No.: WO2004/014256
PCT Pub. Date: Feb. 19, 2004

(65) Prior Publication Data
US 2006/0142833 A1    Jun. 29, 2006

(30) Foreign Application Priority Data
Aug. 7, 2002    (EP) .................... 02017696

(51) Int. Cl.
*A61F 2/06* (2006.01)
(52) U.S. Cl. .................................................. 623/1.11
(58) Field of Classification Search ............. 604/97.01, 604/97.02, 98.01, 99.01, 103.05; 623/1.11; 606/194, 195; 91/392, 400; 222/402
See application file for complete search history.

(56) References Cited

U.S. PATENT DOCUMENTS

| 5,113,608 | A |   | 5/1992 | Hook |
| 5,445,646 | A | * | 8/1995 | Euteneuer et al. ............ 606/198 |
| 6,113,608 | A |   | 9/2000 | Monroe et al. |
| 6,168,617 | B1 |  | 1/2001 | Blaeser et al. |
| 6,736,839 | B2 |  | 5/2004 | Cummings |

FOREIGN PATENT DOCUMENTS

| EP | 1388328 | 2/2004 |
| WO | WO 95/11055 | 4/1995 |
| WO | 00/18330 | 4/2000 |
| WO | 2004/014256 | 2/2004 |

\* cited by examiner

*Primary Examiner*—Todd E Manahan
*Assistant Examiner*—Jennifer L Hornberger
(74) *Attorney, Agent, or Firm*—Workman Nydegger

(57) ABSTRACT

Apparatus for delivering and deploying an expandable stent having a protection sheath within a blood vessel is provided. The apparatus comprises a fluid pressure device that is coupled with a retraction device for the protection sheath, wherein the stent is automatically deployed by the fluid pressure device after retraction of the protection sheath.

14 Claims, 19 Drawing Sheets

APPARATUS FOR DELIVERY AND DEPLOYMENT OF AN EXPANDABLE STENT WITHIN A BLOOD VESSEL

CROSS-REFERENCE TO RELATED APPLICATIONS

The present application claims the benefit of the filing date of International Application PCT/EP2003/008795, filed Aug. 7, 2003, which claims priority from European application 02017696.2, filed Aug. 7, 2002.

FIELD OF THE INVENTION

The present invention relates to an apparatus for delivering and deploying an expandable stent within a blood vessel for use in reinforcing the vessel walls and maintaining the vessel in an open, unobstructed condition.

BACKGROUND OF THE INVENTION

U.S. Pat. No. 6,168,617 discloses a stent delivery system comprising a catheter having a balloon for inflating a stent, which is covered having during delivering. The sheath is axially moveable on the shaft of the catheter and can be retracted in the proximal direction.

U.S. Pat. No. 5,113,608 discloses a stent delivery device comprising a hydraulically actuated retractable sheath. Specifically, a pressurising fluid is supplied by an inflation volume to a portion of a piston housing (or is withdrawn from a portion of the piston housing), thereby actuating the piston and causing the sheath to retract.

In view of the above, it would be desirable to provide an improved stent delivery system having a protection sheath on the stent to simplify handling of the stent.

SUMMARY OF THE INVENTION

In view of the foregoing, it is an object of the present invention to provide an improved stent delivery system having a protection sheath on the stent to simplify handling of the stent.

These and other objects of the present invention are accomplished by providing a device for retracting the sheath that is coupled with a fluid pressure device for inflation and deflation of expandable balloon for deploying the stent. A pressurised fluid is supplied from the fluid pressure device to the retraction device to cause the retraction of the sheath. After or during the retraction of the sheath, the pressurised fluid in is directed to the expandable balloon for expansion and deployment of the stent. The expansion of the stent is controlled by the position of the piston within a cylinder.

The protection sheath is withdrawn by activating the fluid pressure device, which also controls the expansion of the stent. Advantageously, the protection sheath prevents problems associated with bi-stable stent designs, such as stent-loss and pop-open. Additionally, there is no flaring of stainless steel stents and no significantly increased profiles If a drug coated stent is used, there will be substantially no drug loss during handling.

BRIEF DESCRIPTION OF THE SEVERAL VIEWS OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
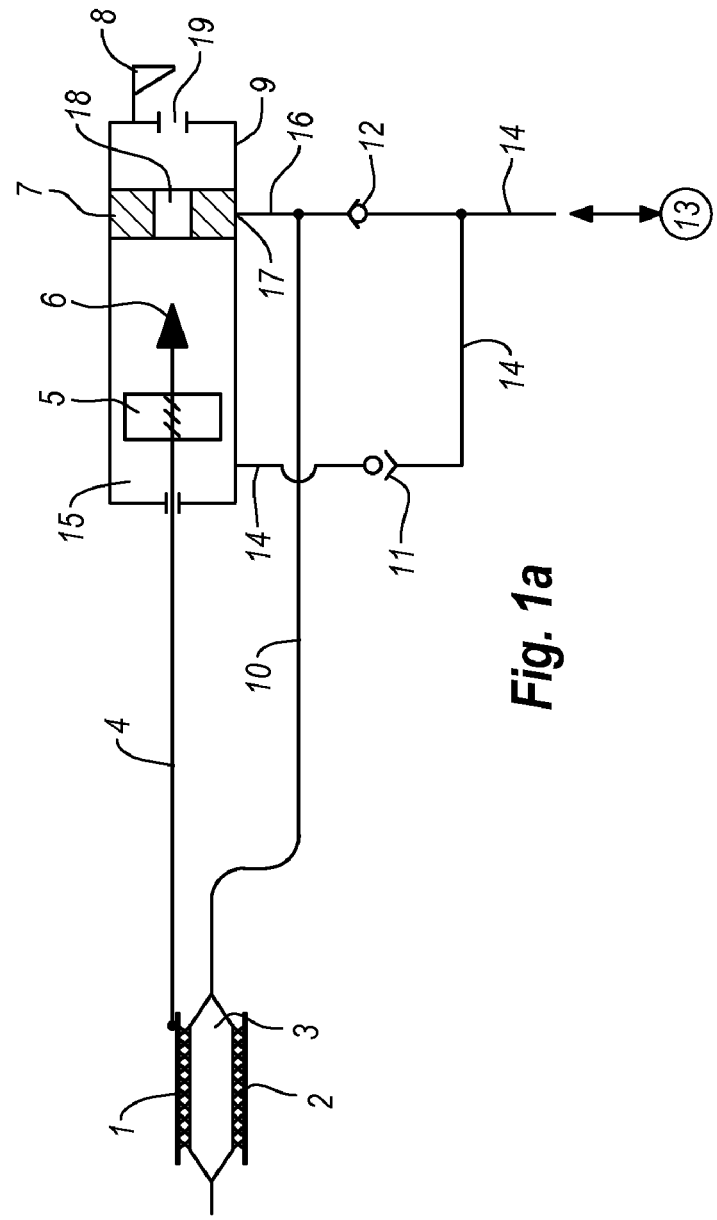
FIGS. 1a and 1b are schematic diagrams of an embodiment of the apparatus for delivering and deploying an expandable stent within a blood vessel, according to the present invention.

Referring to FIG. 1a, sheath 1 is arranged on stent 2 and supported by expandable balloon 3. The sheath, stent and balloon are supported by a catheter (not shown) and inserted into a blood vessel. Sheath retraction device (5-9, 13-15) and fluid pressure device (11-14) are connected with the sheath, stent and balloon by wire 4 and tube 10. Particularly, wire 4 connects sheath 1 with piston 5 disposed in cylinder 15 comprising cylinder housing 9. Hook 6 is connected at the proximal side of piston 5.

Cylinder 15 further comprises floating piston 7 having opening 18, which can be penetrated by hook 6. Floating piston 7 closes outlet 17 in cylinder 15. Tube 10 connects balloon 3 with tube 16 mounted at outlet 17 of cylinder 15. Tube 14 is connected to an inflation/deflation device schematically shown as double-arrow 13 at one end and via unidirectional valve (check valve) 11 with cylinder 15 at the other end. Tube 14 is connected via unidirectional valve (check valve) 12 with tube 10.

In operation, balloon 3 is in a deflated state and sheath 1 covers stent 2. Floating piston 7 is positioned so that opening 17 of cylinder housing 9 is closed. An operator such as a physician applies pressure from inflation/deflation device 13 to tube 14. The pressure shuts unidirectional valve 12 and opens unidirectional valve 11. Thus, the pressurised fluid flows into cylinder 15 and shifts piston 5 with wire 4 and sheath 1 in the proximal direction such that sheath 1 is retracted from stent 2. The pressure necessary for moving piston 5 preferably is very low.

When piston 5 reaches floating piston 7, the proximal end of wire 4 with hook 6 penetrates opening 18 in piston 7, and piston 5 forces piston 7 to move proximally. At the proximal end of cylinder 15, hook 6 engages hook holder 8 such that piston 5, wire 4 and sheath 1 are fixed at the proximal end, as depicted in FIG. 1b. In this position, the sheath is completely removed from the stent, and outlet 17 of cylinder 15 is open towards the cylinder chamber.

In operation, pressurized fluid from inflation/deflation device 13 flows via tube 14 into the left side of cylinder 15. From the cylinder, the pressurized fluid flows through outlet 17, tube 16 and tube 10 to balloon 3. The pressure is applied until a predetermined stent diameter is achieved. Then, the operator applies suction from inflation/deflation device 13 via unidirectional valve 12 and tube 10 to balloon 3. During suction, unidirectional valve 11 is closed. At the end of the stent delivery and deployment process, the catheter is removed from the blood vessel and the stent remains in the desired position within the blood vessel.

Figure 2:
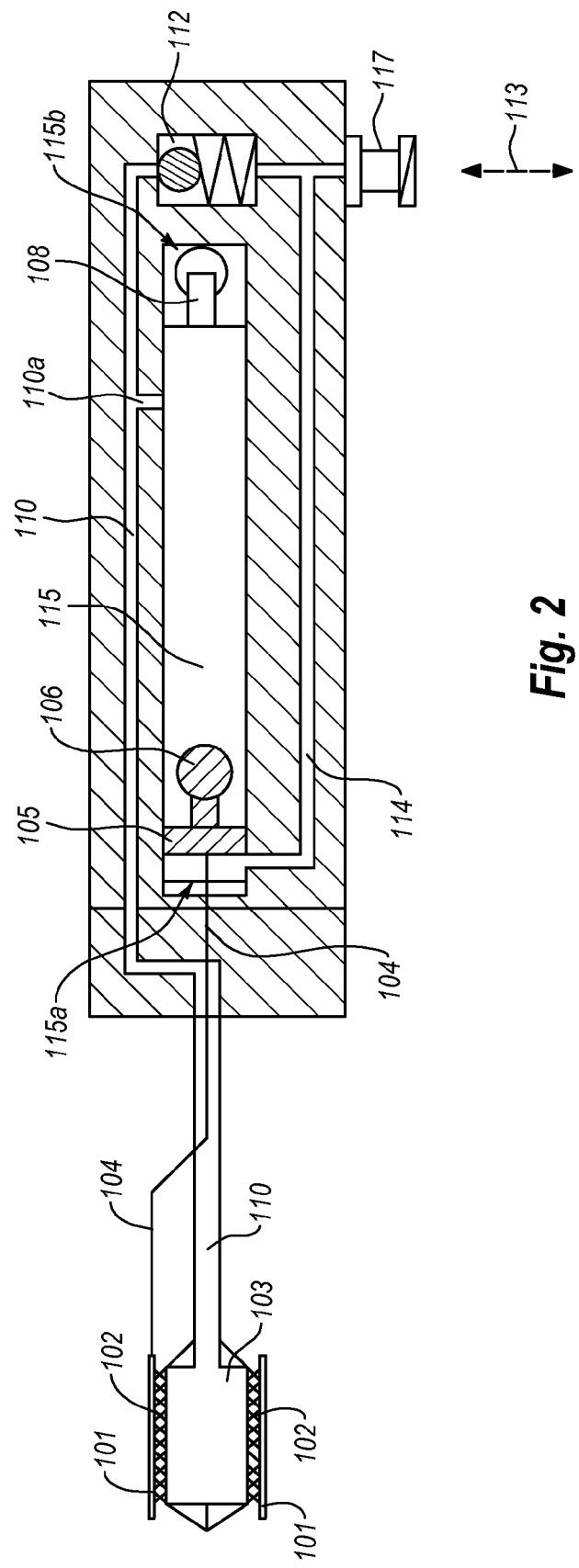
FIG. 2 is a cross-sectional view of another embodiment of the apparatus for delivering and deploying an expandable stent within a blood vessel, according to the present invention.

Referring to FIG. 2, according to another embodiment of the invention, protective cover sheath 101 is arranged on stent 102, which is supported by expandable balloon 103. Similar to the embodiment of FIG. 1, sheath 101, stent 102 and balloon 103 are supported by a catheter (not shown), which is inserted into a blood vessel. Sheath 101, stent 102 and balloon 103 are connected via pull-wire 104 to cylinder-piston arrangement (105, 106, 108, 110, 110a, 112 and 114).

With further reference to FIG. 2, the cylinder-piston arrangement is connected to an inflation/deflation device that is schematically shown as arrow 113. Piston 105 with connector ball 106 is arranged in the cylinder at its distal end 115a. Wire 104 is fixed at the piston. Receiving socket 108 is located at the proximal end 115b of cylinder 115. The connector ball engages receiving socket 108 when the piston arrives at the proximal end of cylinder 115. The cylinder-piston arrangement further comprises unidirectional valve 112, fluid pressure lines 114, 110, 110a and inlet/outlet 117 for inflation/deflation device 113.

Referring to FIGS. 3-10, the steps of operation of the embodiment of FIG. 2 are now described.

Figure 3:
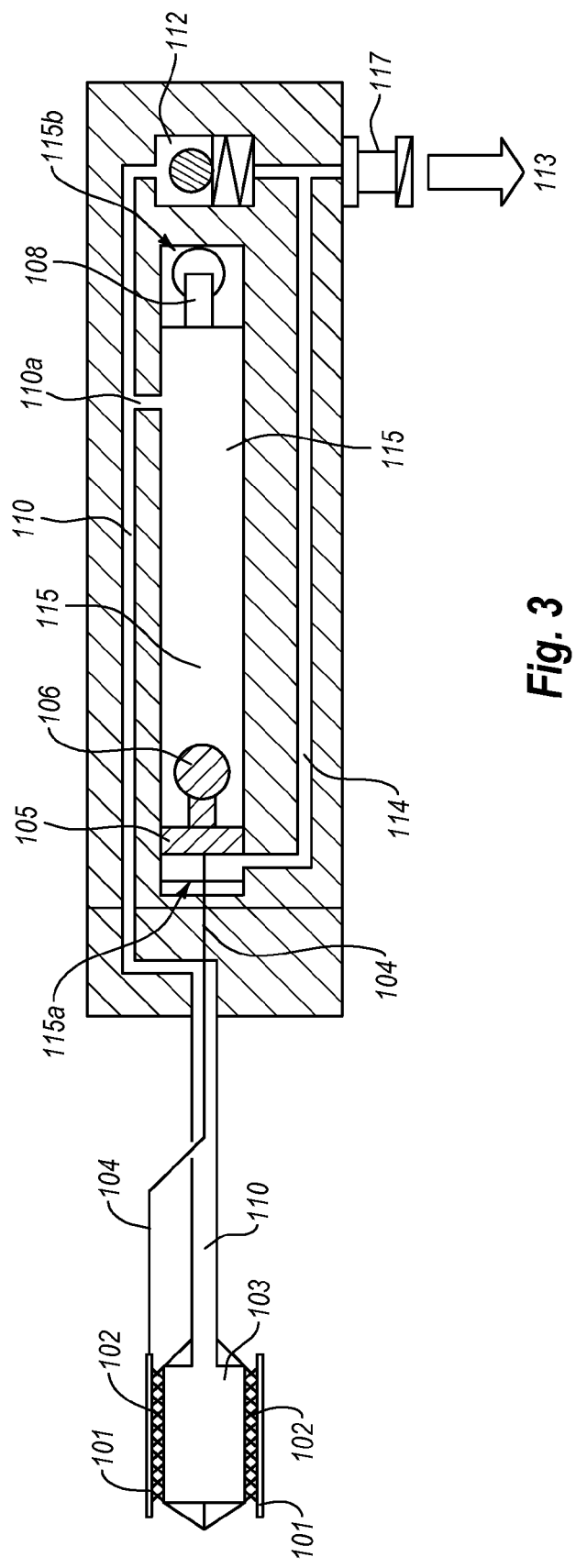
FIGS. 3-10 are cross-sectional views of the apparatus of FIG. 2, showing steps of the method of operation of the apparatus.

Referring to FIG. 3, vacuum from inflation/deflation device 113 is employed to purge air from the catheter and the sheath retraction apparatus. In this state, unidirectional valve 112 is opened and all parts of the apparatus are in connection with the vacuum. After removing the air from the apparatus, pressurized fluid F (e.g., liquid) is introduced from inflation/deflation device 113 via inlet/outlet 117. The fluid is shown in black in the figures for illustrative purposes only.

Figure 4:
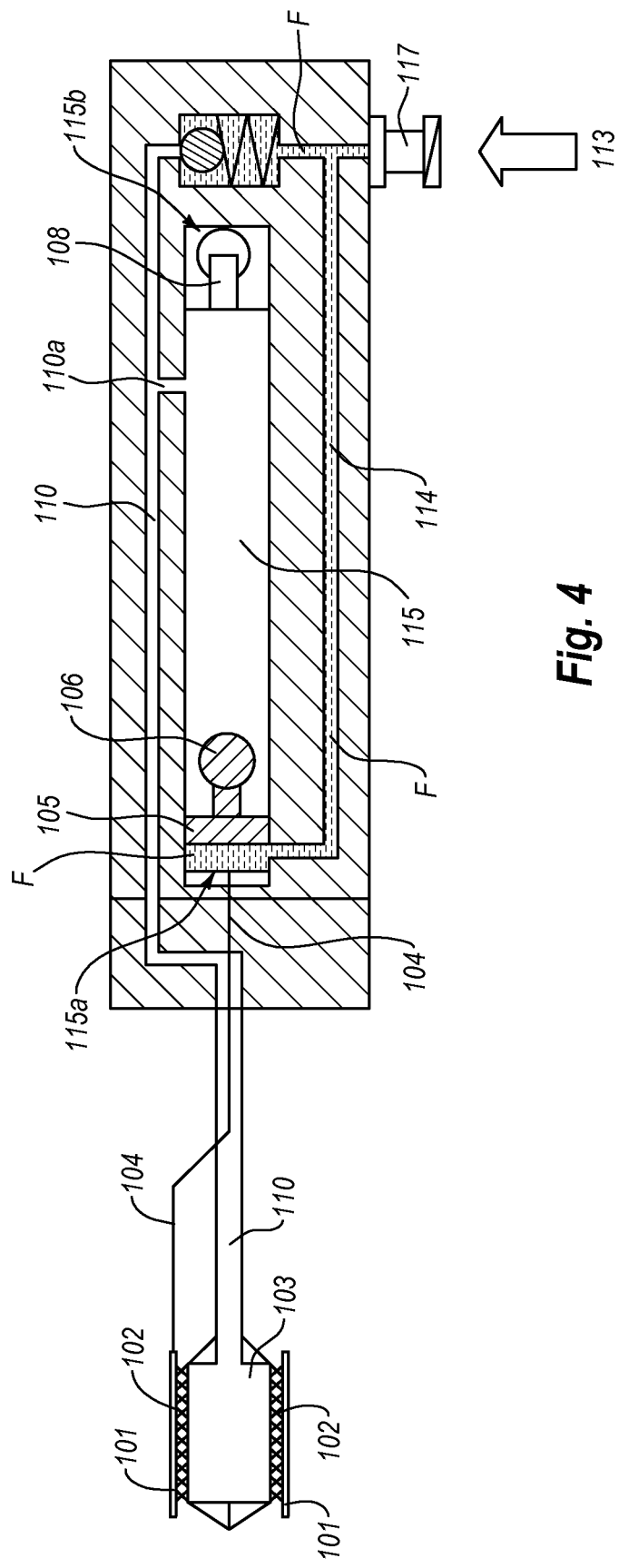
Figure 5:
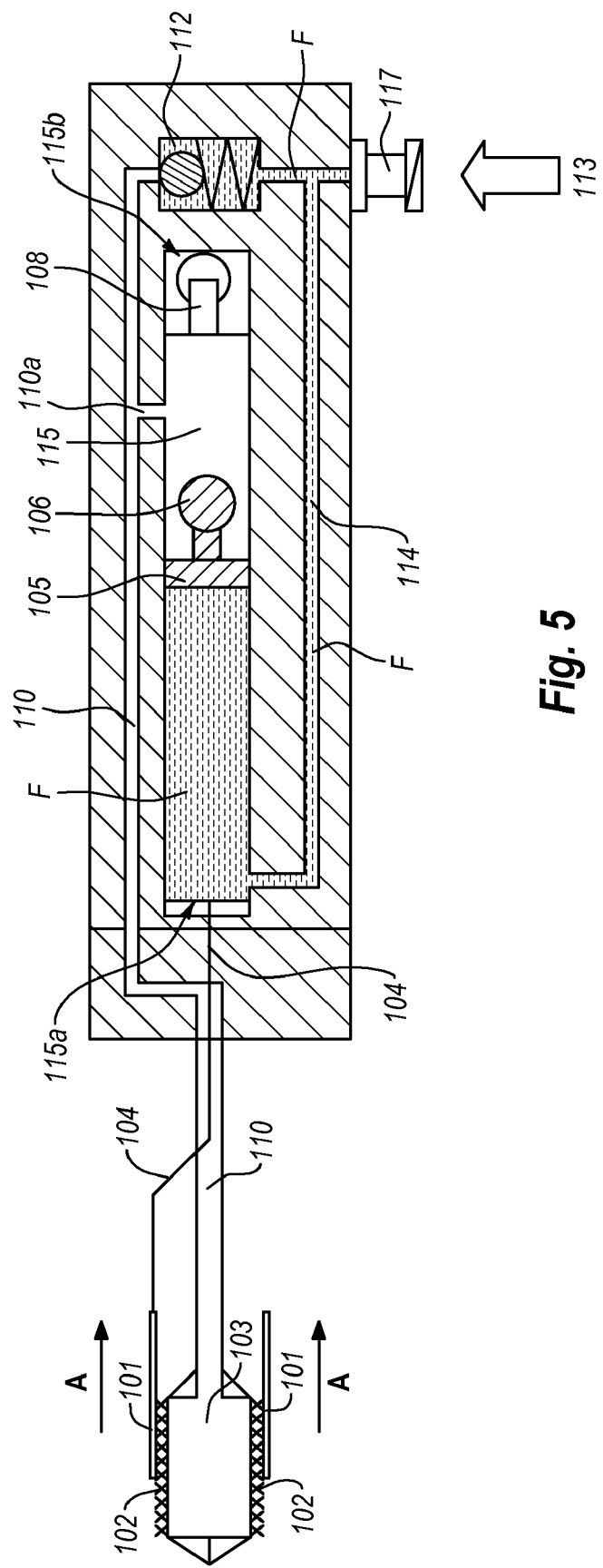

Referring to FIG. 4, the force of pressurized fluid F shuts unidirectional valve 112, and fluid F enters cylinder 115 at its distal end 115a behind piston 105. Referring to FIG. 5, the force of pressurized fluid F moves cylinder 105 in the proximal direction such that wire 104 retracts protective cover sheath 101 from stent 102. During this procedure, the liquid preferably is prevented from entering the catheter and the balloon.

Figure 6:
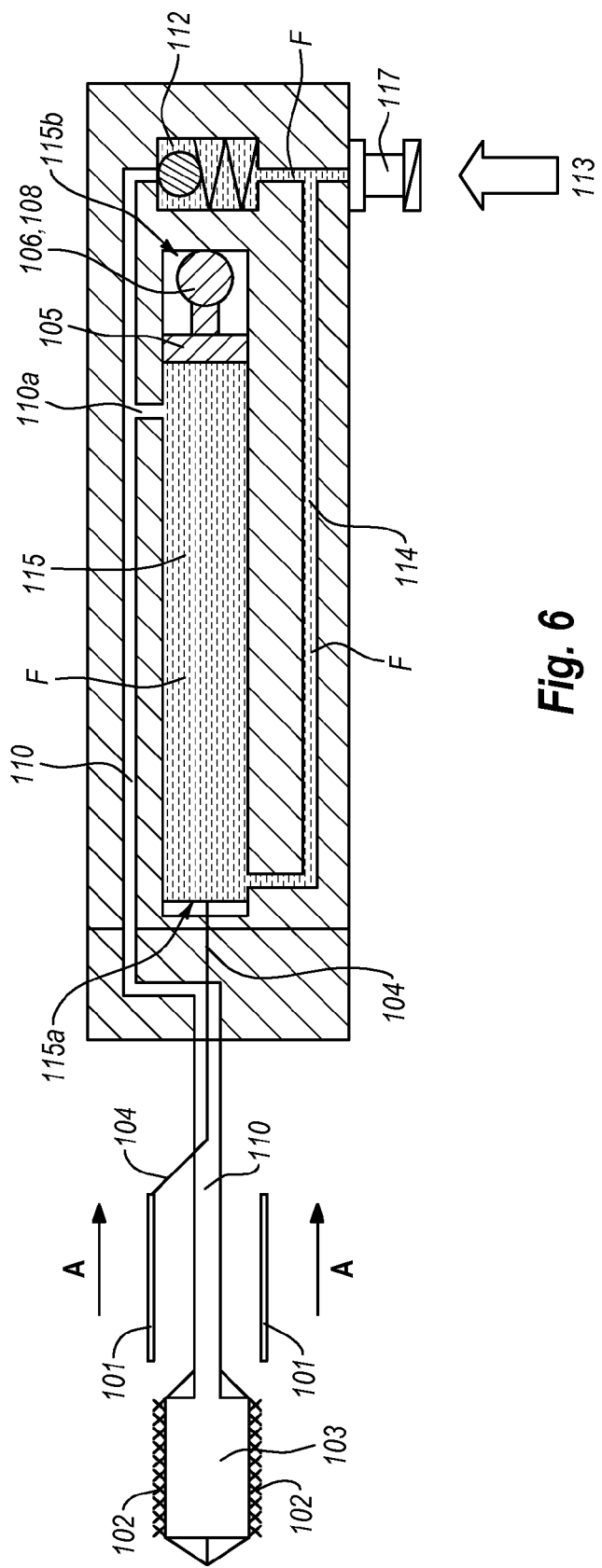
Figure 7:
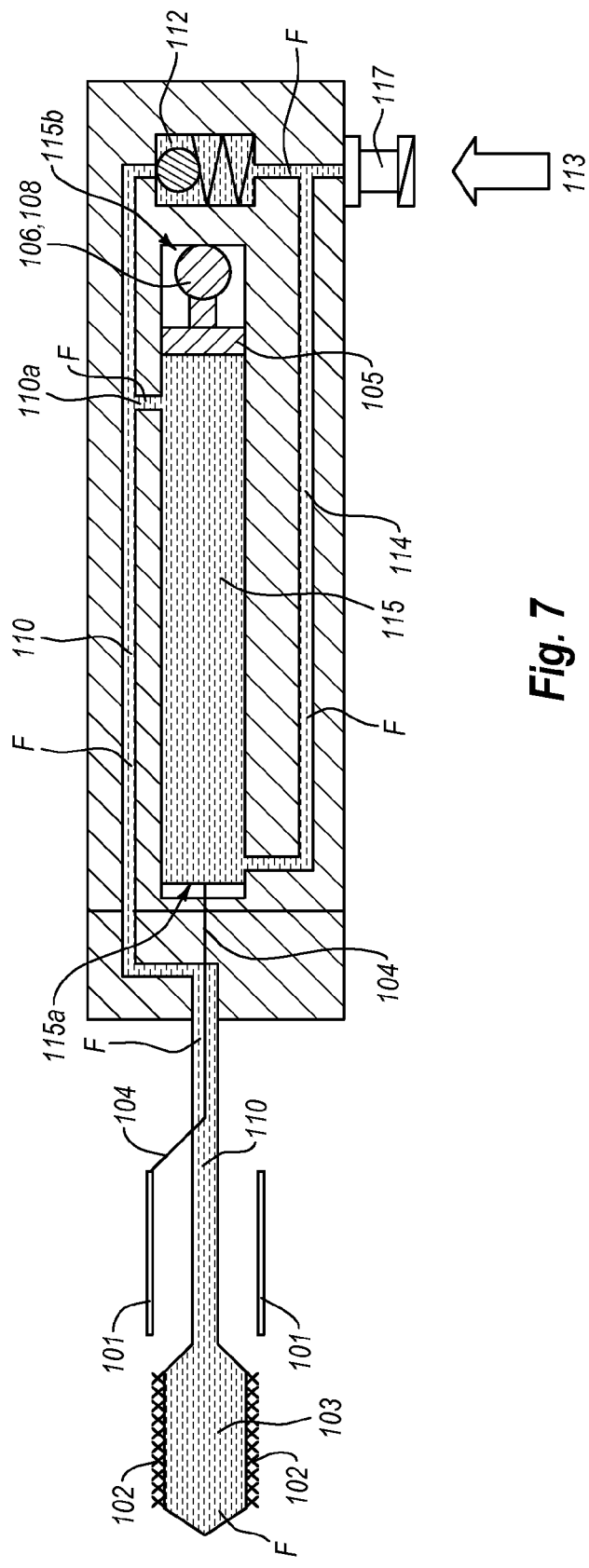

Referring to FIG. 6, after arrival of piston 105 at proximal end 115b of cylinder 115, cover sheath 101 is completely removed from stent 102, connector ball 106 is engaged in receiving socket 108. Also, opening 110a, which penetrates the cylinder wall to the fluid pressure line 110, is opened. The pressurized fluid enters line 110 and inflates the balloon, as depicted in FIG. 7.

Figure 8:
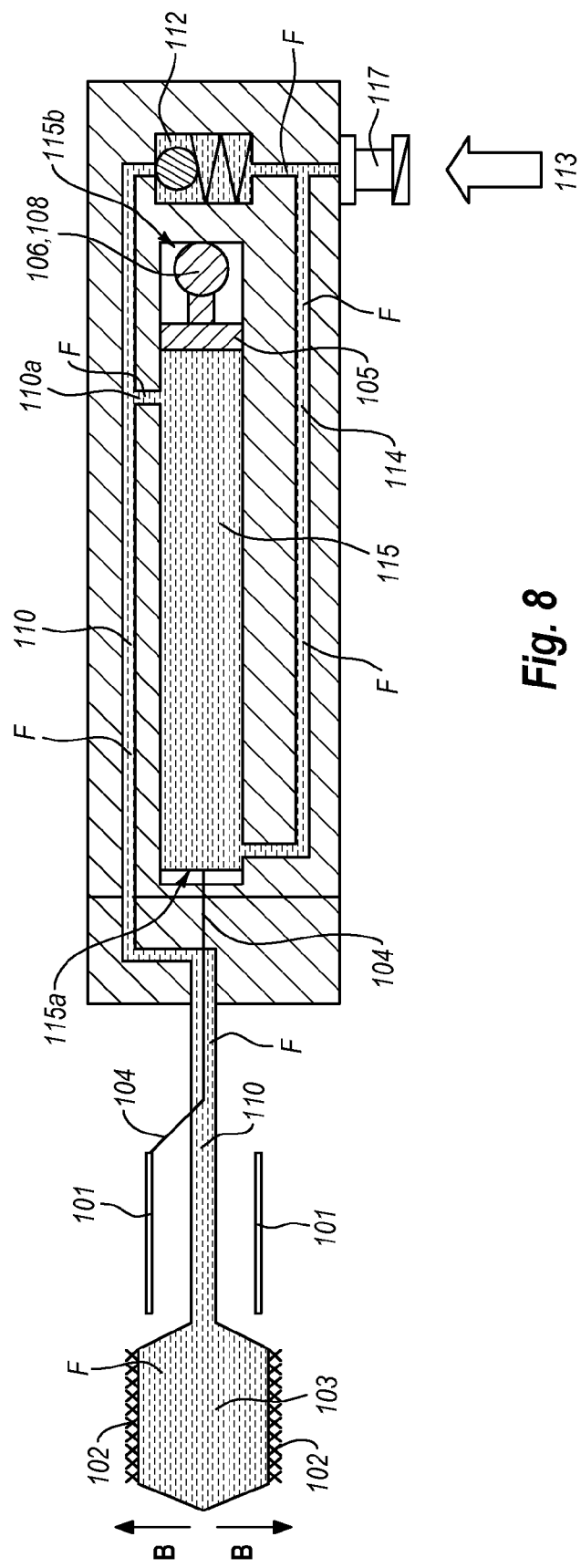
Figure 9:
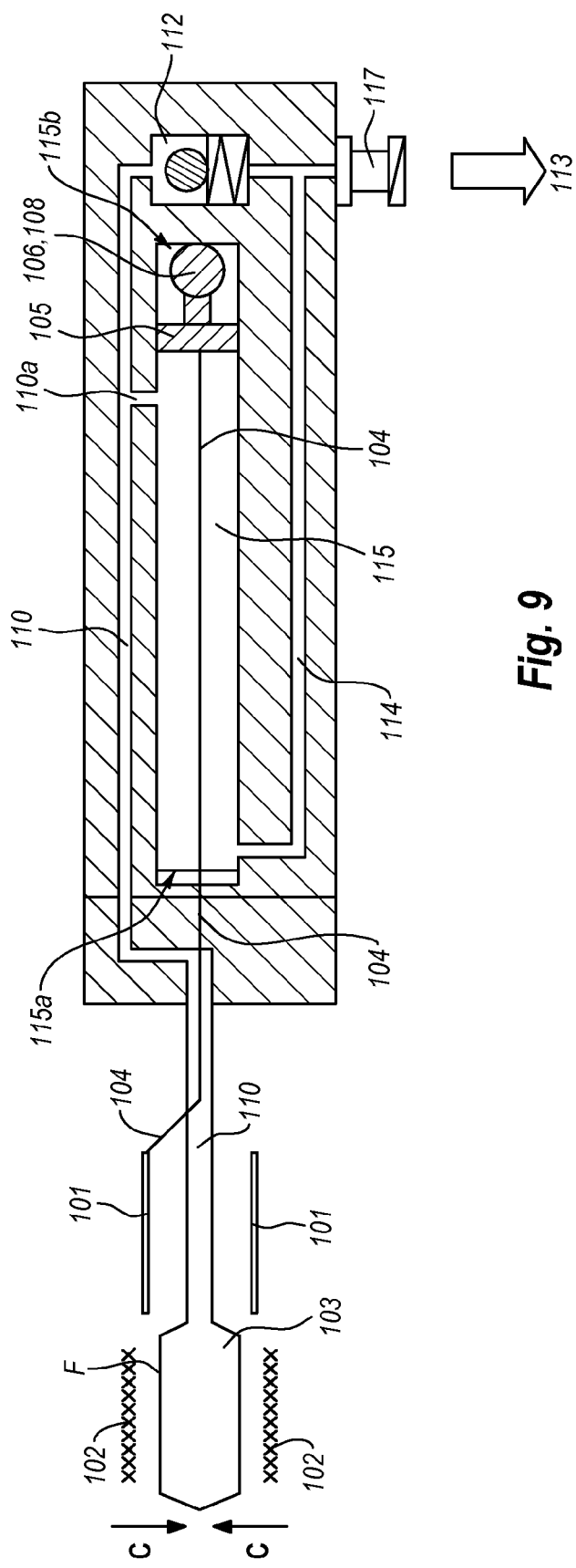
Figure 10:
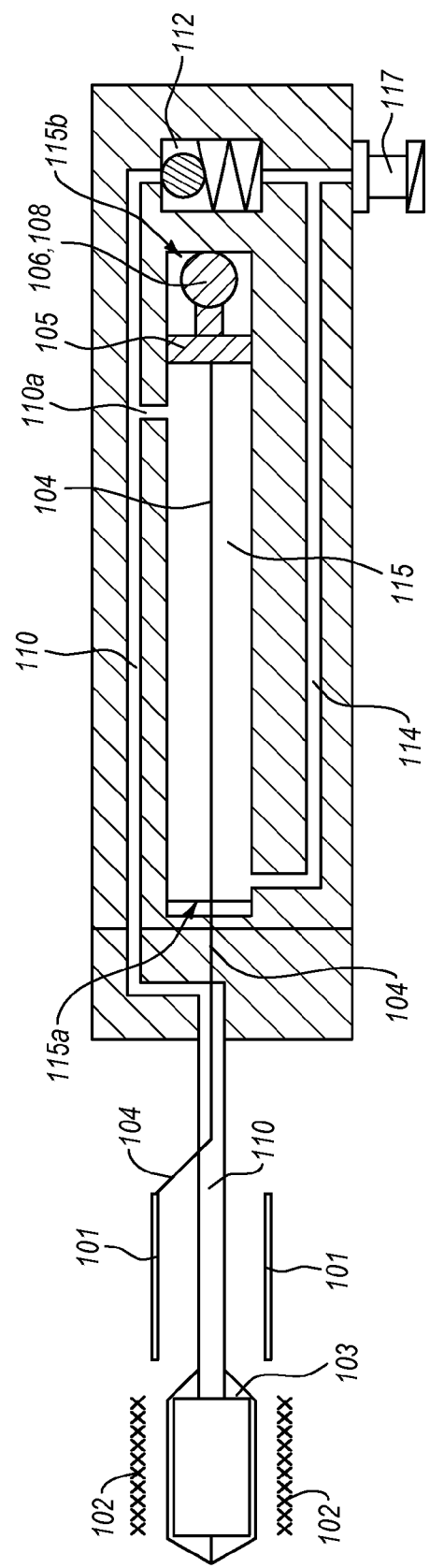

Referring to FIG. 8, the balloon expands and stent 102 is deployed and contacts the wall of the blood vessel. Thereafter, the fluid is withdrawn and a vacuum is again applied by means of inflation/deflation device 113 to deflate the balloon while piston 105 and cover sheath 101 remain fixed, as depicted in FIG. 9. Referring to FIG. 10, the system is fully purged of fluid and balloon 103 can be re-inflated if necessary, or the balloon and sheath may be removed from the blood vessel while the stent remains in the desired position within the blood vessel.

Figure 11:
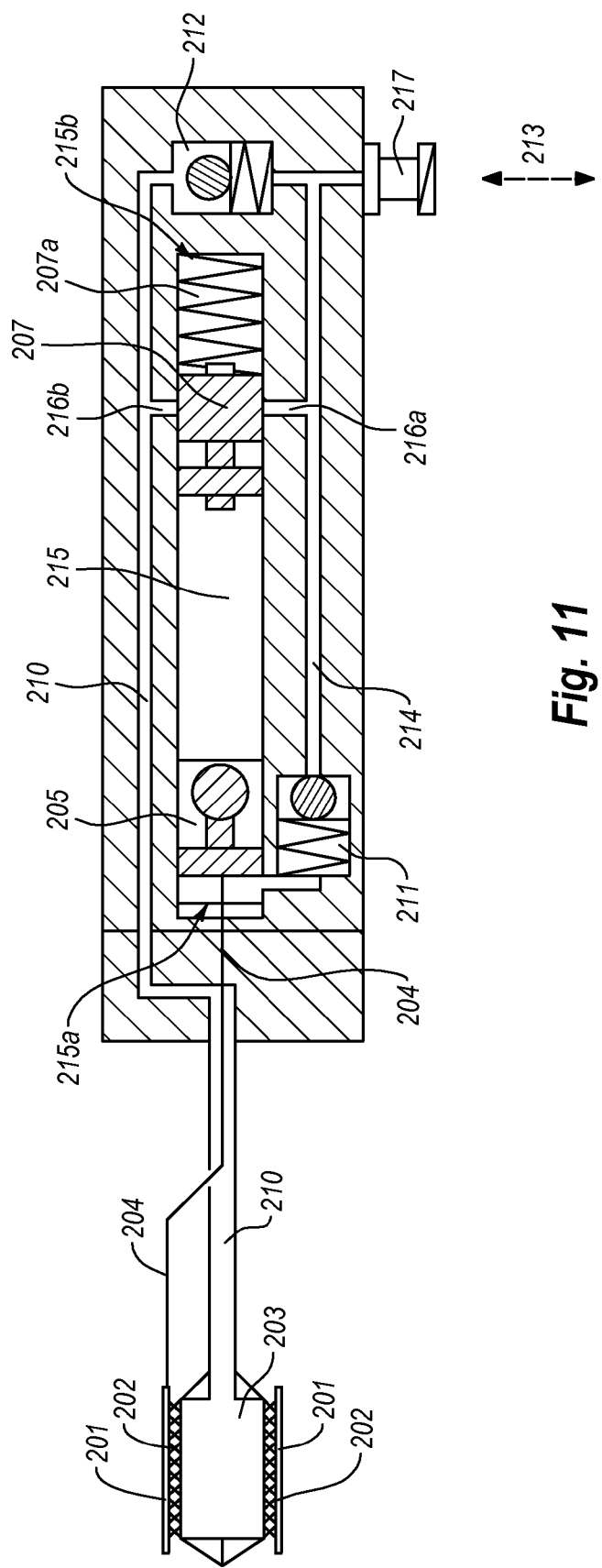
FIG. 11 is a cross-sectional view of a further embodiment of the apparatus for delivering and deploying an expandable stent within a blood vessel, according to the present invention.
Figure 12:
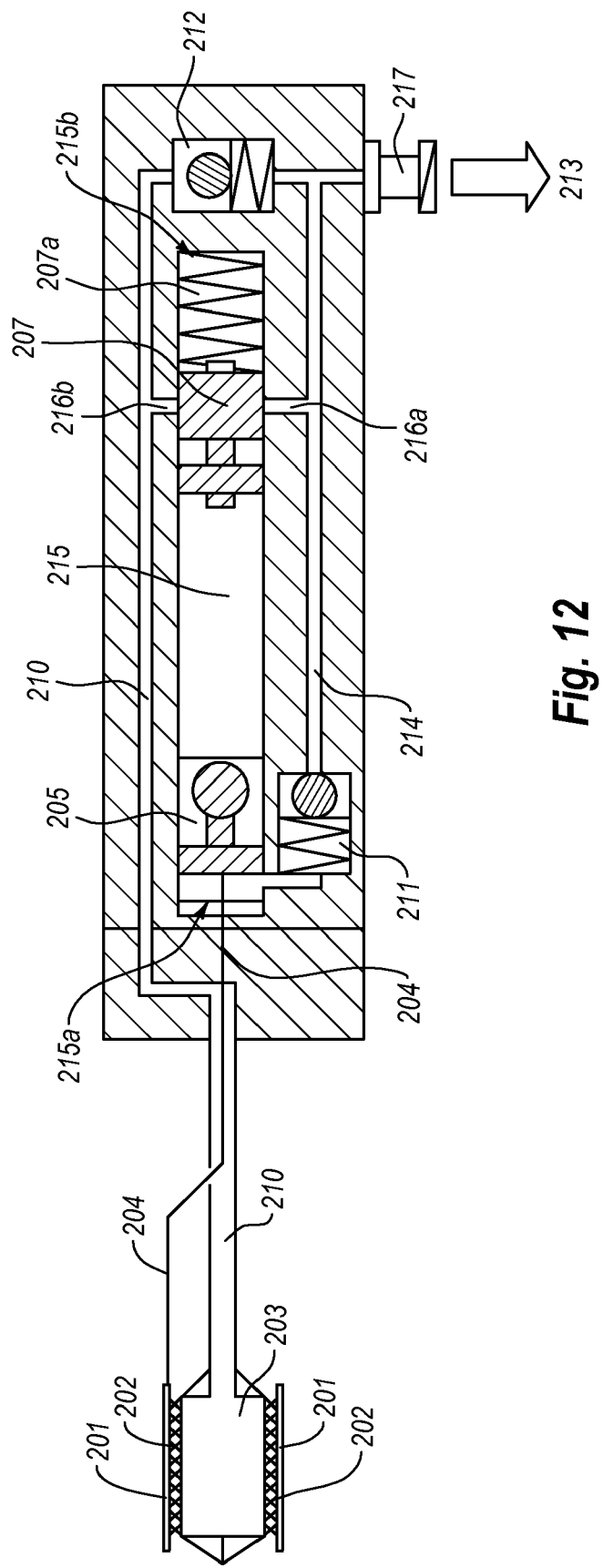
FIGS. 12-19 are cross-sectional views of the apparatus of FIG. 11, showing steps of the method of operation of the apparatus.

Referring to FIG. 11, a further embodiment of the present invention is described. Two-position valve 207 is located in cylinder 215, wherein valve 207 abuts spring 207a disposed at the proximal end 215b of cylinder 215. In the illustrated embodiment, valve 207 shuts a pair of channels 216a, 216b, which penetrate the wall of the cylinder 215.

Channel 216a connects fluid pressure line 214 with fluid pressure line 210, which supplies the fluid pressure to balloon 203. When the piston 205 is disposed at two-position valve 207, it pushes the valve proximally and opens channels 216a and 216b. Thus, pressurized fluid F from inflation/deflation device 213 enters balloon 203 via line 214, channels 216a and 216b and line 210.

Referring to FIGS. 12-19, the steps of the method of operation of the embodiment of FIG. 11 are now described.

Figure 13:
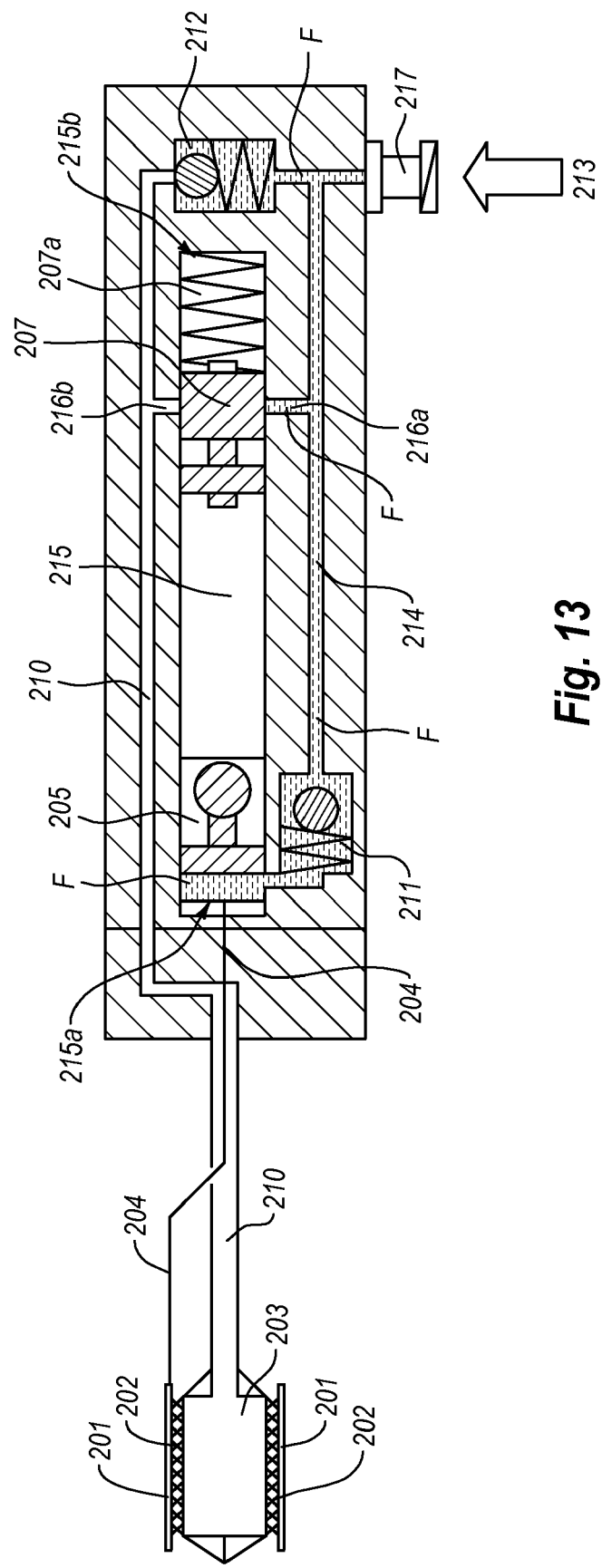
Figure 14:
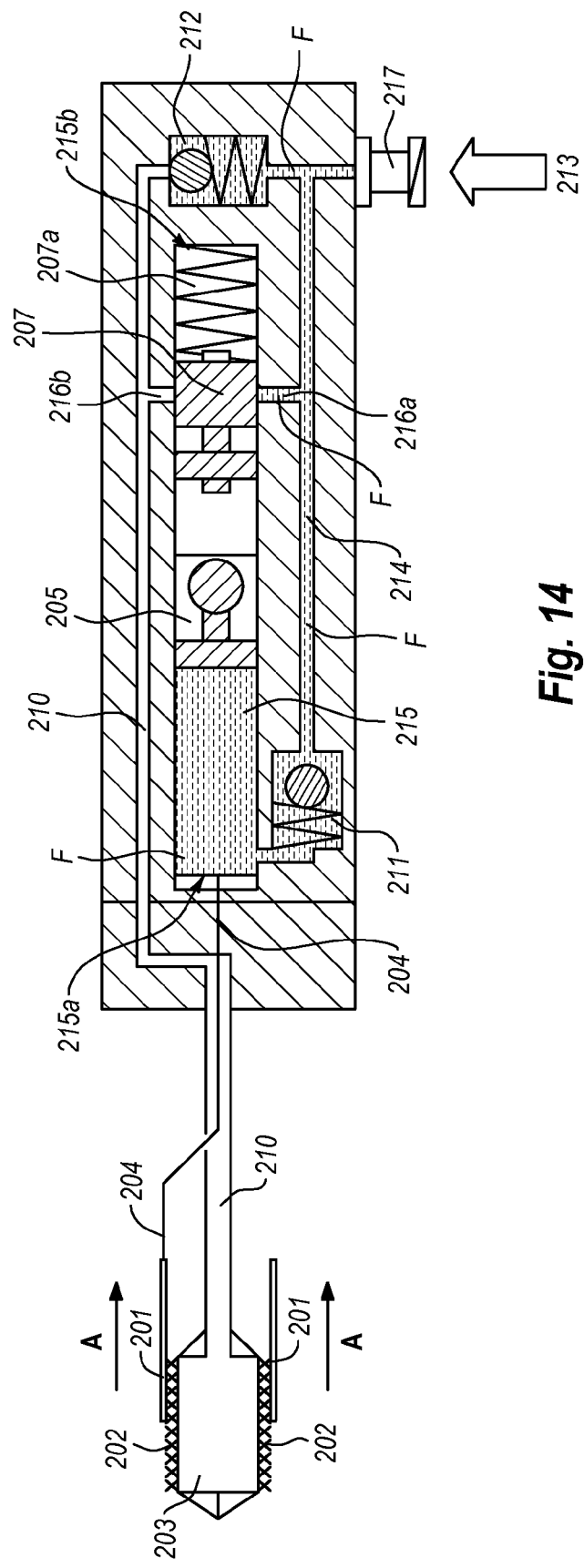

Initially, a vacuum is applied in order to purge air from the catheter and the sheath retraction apparatus by means of inflation/deflation device 213. Specifically, unidirectional valve 212 is opened and unidirectional valve 211 is closed so that space 215a at the distal end of cylinder 215 remains open. Referring to FIG. 13, while unidirectional valve 212 and channels 216a and 216b are closed, pressurized fluid F from inflation/deflation device 213 enters space 215a of cylinder 215 behind piston 205 via line 214 and unidirectional valve 211. Thereafter, piston 205 moves in the proximal direction, thereby retracting protective cover sheath 201 from stent 202 in the direction of arrows A, as depicted in FIG. 14.

Figure 15:
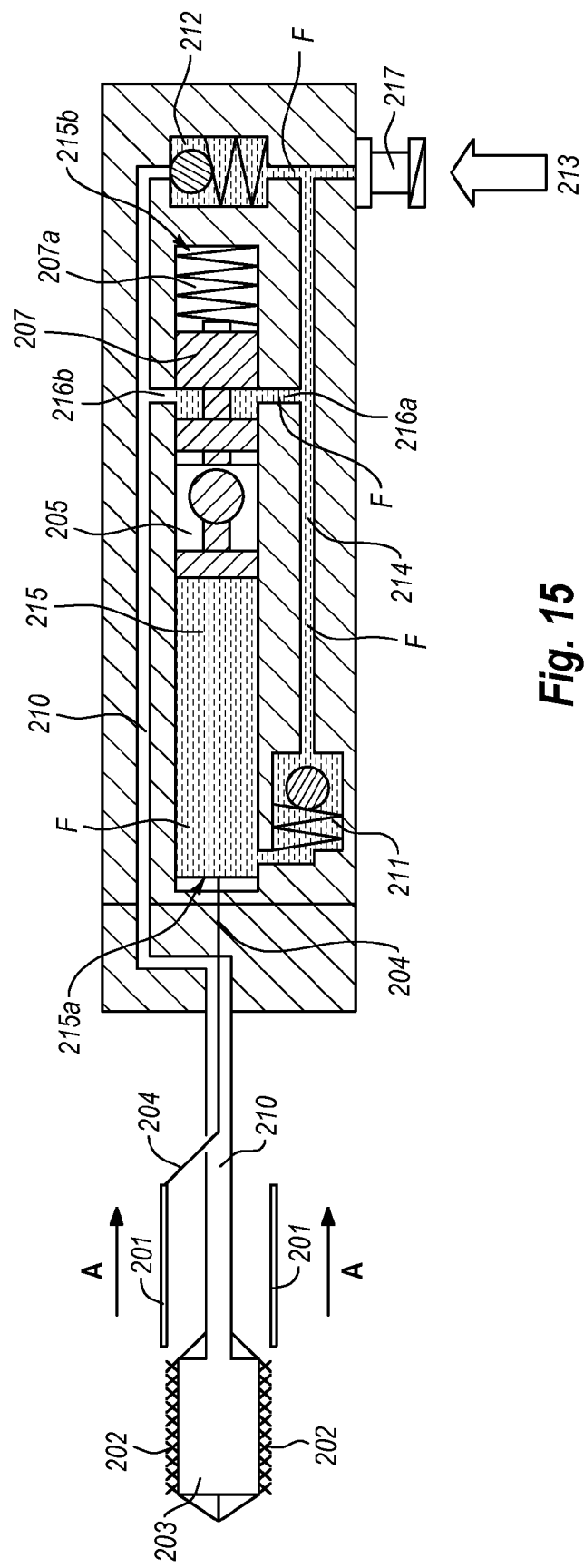
Figure 16:
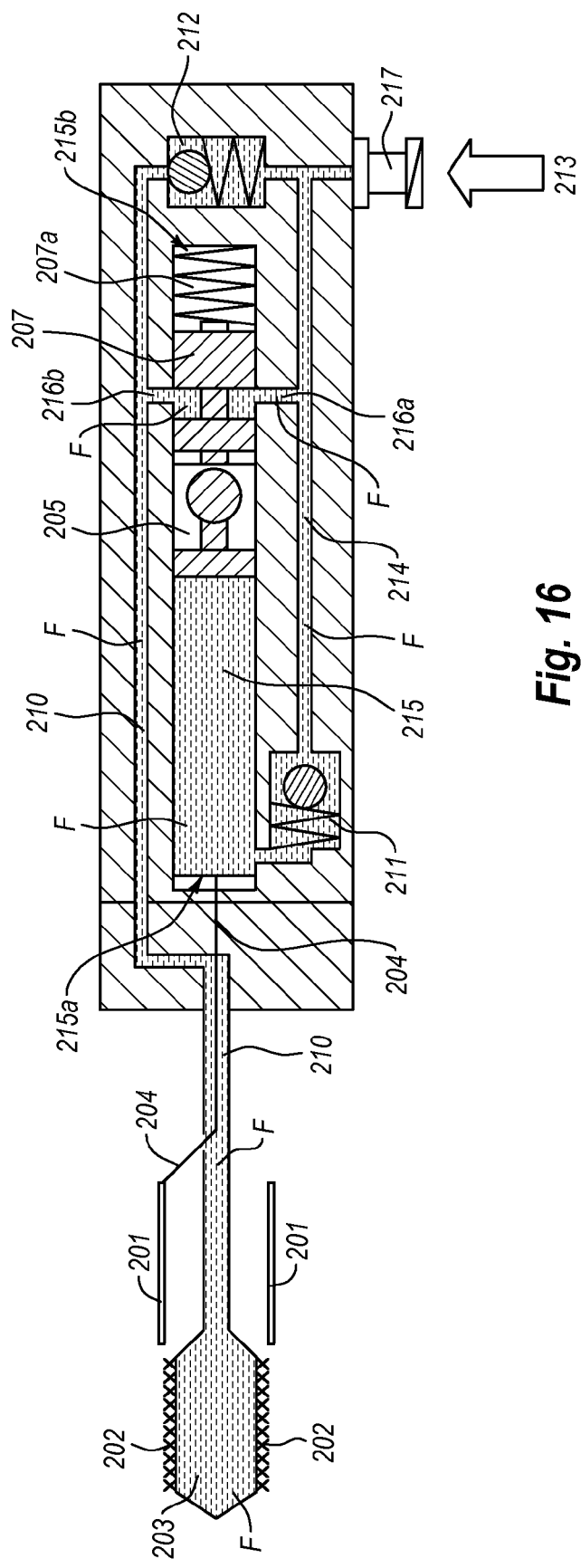
Figure 17:
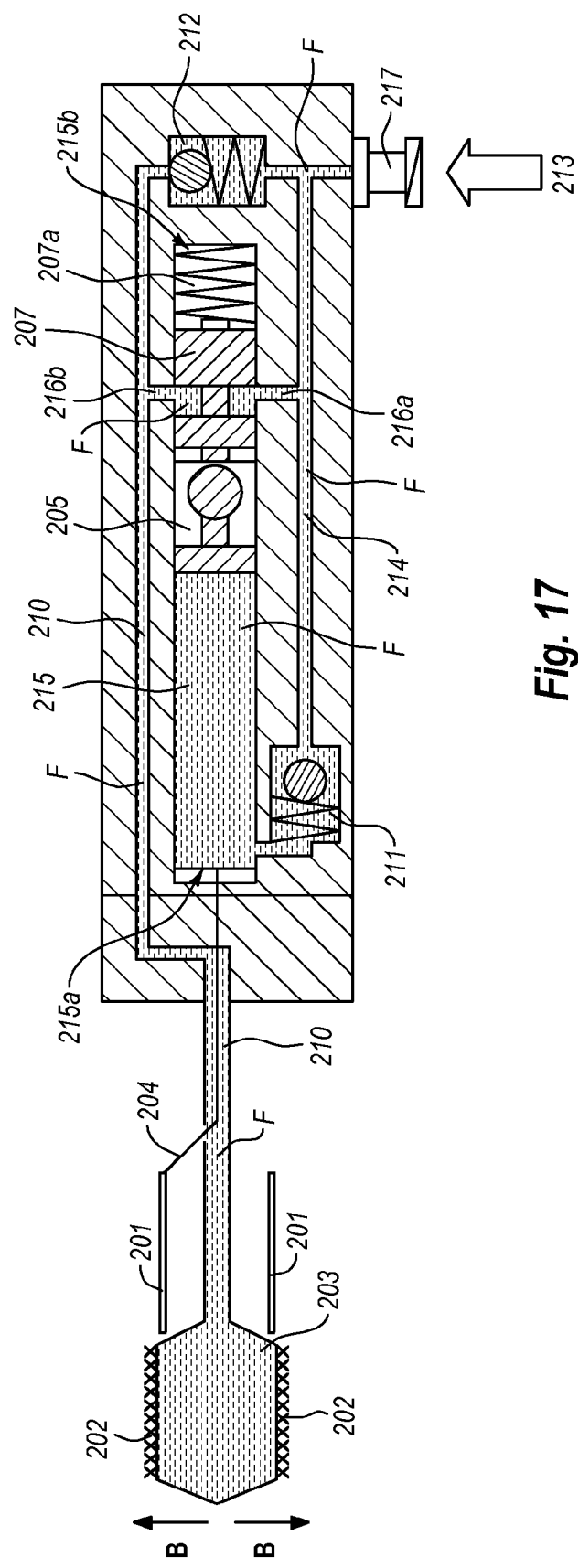

Referring to FIG. 15, after protective cover sheath 201 is fully retracted, piston 205 pushes valve 207 into an open position against the force of spring 207a, and the connection between line 214 and line 210 via channels 216a and 216b is opened. Referring to FIG. 16, pressurized fluid F flows via line 214, channels 216a and 216b and line 210 to balloon 203. While unidirectional valve 211 remains open and pressurized fluid F acts against piston 205, two-position valve 207 remains in the open position. Referring to FIG. 17, balloon 203 expands in the direction of arrows B and the stent is deployed such that it contacts the wall of the blood vessel.

Figure 18:
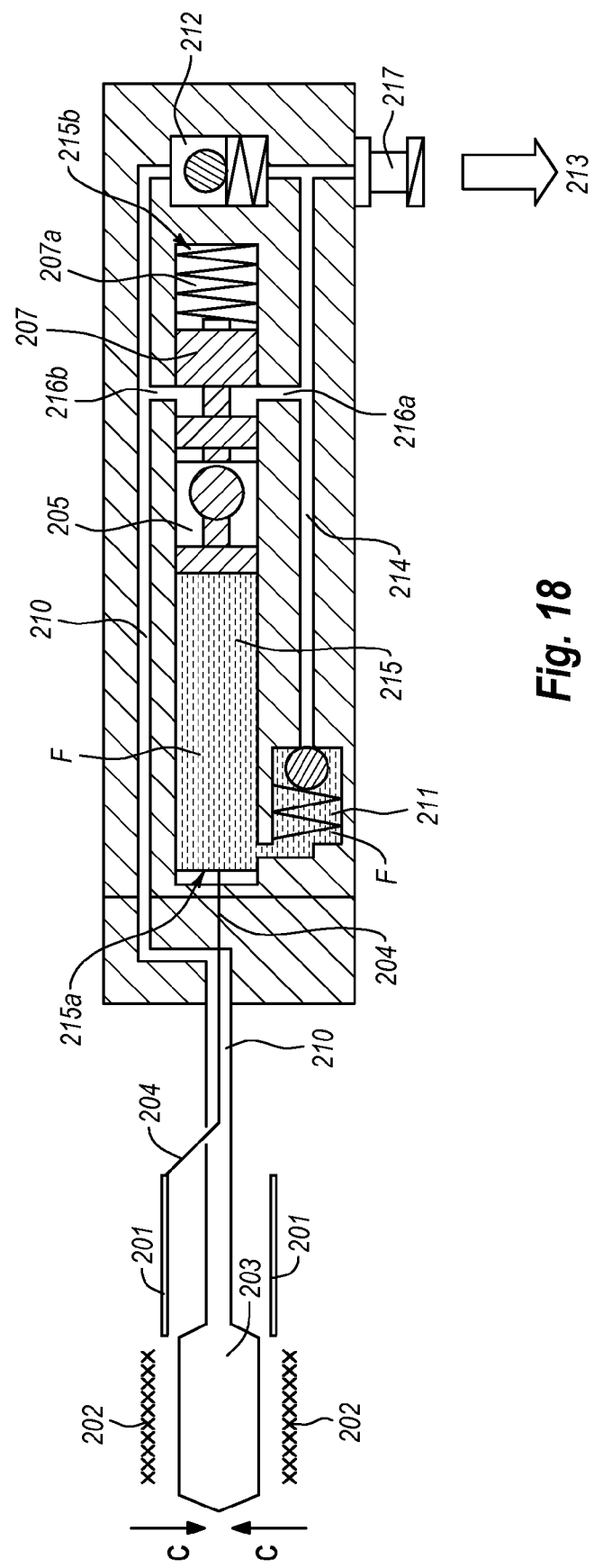
Figure 19:
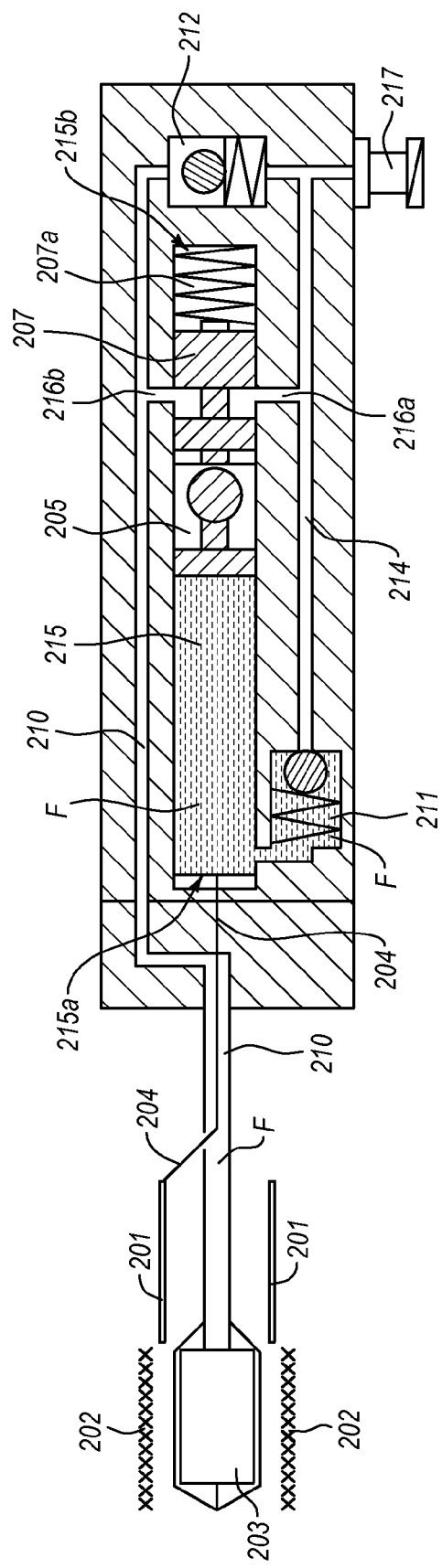

Thereafter, vacuum is again applied from inflation/deflation device 213 and balloon 203 deflates in the direction of arrows C, as depicted in FIG. 18. The unidirectional valve is closed and the pressurized fluid behind piston 205 acts on piston 205 such that piston 205 and sheath 201 remain fixed. Referring to FIG. 19, the catheter is fully purged and the balloon can be re-inflated if necessary. The pressurized fluid holds two-position valve 207 open and locks sheath 201 in the retracted position. If the retraction apparatus will be used one time only, it can be removed. However, if the retraction apparatus will be re-used, fluid F is purged from cylinder 215 by opening unidirectional valve 211 and pulling piston 205 to distal end 215a.

The fluid pressure for operating the retraction device and the expandable means can be controlled in such a manner that the retraction device and the balloon work concurrently or sequentially in order to control the correct position of the stent.

According to a preferred implementation of the invention, the retraction of the sheath automatically controls the deployment of the stent. Therefore, an operator may deploy the stent by activating the inflation/deflation device.

The invention claimed is:

1. An apparatus for delivery and deployment of an expandable stent within a vessel, the apparatus comprising:

a catheter having a proximal end and a distal end, an expandable means mounted at the distal end of the catheter and being expandable by means of a fluid pressure device and a liquid fluid, the expandable means being expandable from a delivery diameter to a deployment diameter, a sheath being slidably mounted over the expandable means and being arranged for proximal retraction from over the expandable means by means of a retraction device, the refraction device comprises a cylinder-piston arrangement operated by the fluid pressure of the liquid, the cylinder-piston arrangement comprises an outlet connected to a fluid pressure line for applying the fluid pressure to the expandable means, the fluid pressure device is further arranged for operating the retraction device so that the expandable means is expanded in response to the retraction of the sheath.

2. The apparatus according to claim 1, further comprising a control means for controlling the fluid pressure operating the retraction device and the expandable means, either concurrently or sequentially.

3. The apparatus according to claim 1, wherein a first piston of the cylinder-piston arrangement is connected to the sheath via a wire.

4. The apparatus according to claim 3, wherein the cylinder-piston arrangement comprises the first piston and a two-position valve abutting via a spring at the proximal end of the cylinder, wherein in a closed position the valve shuts by the spring force channels penetrating the wall of the cylinder, and in an open position, the valve opens the channels after it is pushed by the piston when the sheath is retracted and connects a fluid pressure line from the fluid pressure device with a fluid pressure line so that the fluid pressure is applied to the expandable means.

5. An apparatus for delivery and deployment of an expandable stent within a vessel, the apparatus comprising:
   a catheter having a proximal end and a distal end,
   an expandable means mounted at the distal end of the catheter and being expandable by means of a fluid pressure device, the expandable means being expandable from a delivery diameter to a deployment diameter,
   a sheath being slidably mounted over the expandable means and being arranged for proximal retraction from over the expandable means by means of a retraction device wherein the refraction device comprises a cylinder-piston arrangement operated by the fluid pressure, and
   the fluid pressure device is further arranged for operating the retraction device so that the expandable means is expanded in response to the retraction of the sheath,
   wherein the cylinder-piston arrangement comprises an outlet connected to a fluid pressure line for applying the fluid pressure to the expandable means.

6. The apparatus according to claim 5, wherein the cylinder-piston arrangement comprises a first piston and a floating second piston for controlling the opening/closing of the outlet.

7. The apparatus according to claim 6, wherein during refraction of the sheath either the first piston or the second piston closes the outlet, and after at least partial retraction of the sheath the first and second pistons are in a position at the proximal end of the cylinder and the outlet is open.

8. The apparatus according to claim 7, wherein the first piston comprises a hook, the second piston comprises a first central opening, the cylinder comprises a second opening and a hook holder at its proximal end, so that during retraction of the sheath the shifting first piston moves the hook through the first opening and the second opening until the hook engages the hook holder.

9. The apparatus according to claim 5 wherein a first piston arrangement comprises a connector means and the cylinder comprises at its proximal end a receiving means for the connector means, so that after retraction of the sheath the connector means engages the receiving means and the outlet is in connection with the fluid pressure acting on the first piston.

10. A system for delivery and deployment of an expandable stent within a vessel, the apparatus comprising:
    a catheter having a proximal end and a distal end,
    an expandable means mounted at the distal end of the catheter and being expandable by means of a fluid pressure device;
    an expandable stent being expandable from a delivery diameter to a deployment diameter, the expandable stent being mounted on the catheter over the expandable means; and
    a sheath being slidably mounted on the stent and being arranged for proximal retraction to expose the stent by means of a retraction device, the refraction device comprising a cylinder-piston arrangement operated by fluid pressure from the fluid pressure device, the cylinder-piston arrangement comprising an outlet connected to a fluid pressure line for applying the fluid pressure to the expandable means, the fluid pressure device is further arranged for operating the refraction device so that the expandable means is expanded in response to the retraction of the sheath.

11. The system according to claim 10, wherein the cylinder-piston arrangement comprises a first piston and a floating second piston for controlling the opening/closing of the outlet.

12. The apparatus according to claim 11, wherein during retraction of the sheath either the first piston or the second piston closes the outlet, and after at least partial retraction of the sheath the first and second pistons are in a position at the proximal end of the cylinder and the outlet is open.

13. The apparatus according to claim 12, wherein the first piston comprises a hook, the second piston comprises a first central opening, the cylinder comprises a second opening and a hook holder at its proximal end, so that during retraction of the sheath the shifting first piston moves the hook through the first opening and the second opening until the hook engages the hook holder.

14. The apparatus according to claim 10 wherein a first piston arrangement comprises a connector means and the cylinder comprises at its proximal end a receiving means for the connector means, so that after refraction of the sheath the connector means engages the receiving means and the outlet is in connection with the fluid pressure acting on the first piston.

* * * * *